US011213667B2

(12) United States Patent
Mobed-Miremadi et al.

(10) Patent No.: US 11,213,667 B2
(45) Date of Patent: Jan. 4, 2022

(54) 3D PRINTED MICRONEEDLES FOR MICROENCAPSULATED MAMMALIAN CELL EXTRUSION

(71) Applicants: Maryam Mobed-Miremadi, Sunnyvale, CA (US); Chantell Farias, San Jose, CA (US); Cecilia Hemingway, San Francisco, CA (US); Roman Lyman, San Francisco, CA (US)

(72) Inventors: Maryam Mobed-Miremadi, Sunnyvale, CA (US); Chantell Farias, San Jose, CA (US); Cecilia Hemingway, San Francisco, CA (US); Roman Lyman, San Francisco, CA (US)

(73) Assignee: Santa Clara University, Santa Clara, CA (US)

( * ) Notice: Subject to any disclaimer, the term of this patent is extended or adjusted under 35 U.S.C. 154(b) by 186 days.

(21) Appl. No.: 16/509,114

(22) Filed: Jul. 11, 2019

(65) Prior Publication Data
US 2021/0008359 A1    Jan. 14, 2021

Related U.S. Application Data

(60) Provisional application No. 62/696,410, filed on Jul. 11, 2018.

(51) Int. Cl.
*A61M 37/00* (2006.01)
*B33Y 80/00* (2015.01)

(52) U.S. Cl.
CPC ......... *A61M 37/0015* (2013.01); *B33Y 80/00* (2014.12); *A61M 2037/003* (2013.01);
(Continued)

(58) Field of Classification Search
CPC .... A61M 2037/0023; A61M 2037/003; A61M 2037/0053; A61M 2037/0046;
(Continued)

(56) References Cited

U.S. PATENT DOCUMENTS 7,537,590 B2    5/2009  Santini, Jr
8,684,968 B2    4/2014  Genosar
(Continued)

FOREIGN PATENT DOCUMENTS

CN         105073102 A  * 11/2015  ............. A61K 38/28
WO     WO-9921481 A2  *  5/1999  ........ A61M 5/14546
(Continued)

*Primary Examiner* — Deanna K Hall
(74) *Attorney, Agent, or Firm* — Lumen Patent Firm

(57) ABSTRACT

A 3D printed biocompatible drug delivery device is provided having a fluid delivery channel distinguishing three segments and a receiving chamber with an array of microneedles. The three segments of the delivery channel are stagnation zones before a drug is extruded and whereby an inverted funnel provides an increasing extrusion surface servicing the drug to the array of microneedles. The design of the device with its flow-related components circumvents the challenge of colloidal stability associated with multiphase formulations leading to nozzle blockage. Qualitative screening cytotoxicity tests pre and post-extrusion through the drug delivery device using mammalian cells rule out cytotoxicity and outline equivalent viability to control treatments. The biocompatibility results suggest that the fluid delivery design, the photoresin selected as well as the fabrication and sterilization may be extended over a range of regenerative medicine and drug delivery applications.

17 Claims, 13 Drawing Sheets

(52) U.S. Cl.
CPC .............. *A61M 2037/0023* (2013.01); *A61M 2037/0053* (2013.01); *A61M 2209/02* (2013.01)

(58) Field of Classification Search
CPC ........ A61M 2037/0061; A61M 5/3295; A61M 2037/0038; A61M 37/0015; A61M 2209/02; B33Y 80/00
See application file for complete search history.

(56) References Cited

U.S. PATENT DOCUMENTS

| | | | | |
|---|---|---|---|---|
| 2003/0009113 | A1* | 1/2003 | Olson | A61B 5/150984 600/573 |
| 2007/0161964 | A1* | 7/2007 | Yuzhakov | A61M 37/0015 604/272 |
| 2009/0234322 | A1* | 9/2009 | Fischer | A61M 5/346 604/512 |

FOREIGN PATENT DOCUMENTS

| | | | | |
|---|---|---|---|---|
| WO | WO-0205890 A2 * | 1/2002 | ........... | A61B 17/205 |
| WO | WO-2018069543 A1 * | 4/2018 | ............. | A61B 17/08 |

* cited by examiner

3D PRINTED MICRONEEDLES FOR MICROENCAPSULATED MAMMALIAN CELL EXTRUSION

CROSS-REFERENCE TO RELATED APPLICATIONS

This application claims priority from U.S. Provisional Patent Application 62/696,410 filed Jul. 11, 2018, which is incorporated herein by reference.

FIELD OF THE INVENTION

The invention relates to 3D printed microneedles for cell extrusion.

BACKGROUND OF THE INVENTION

Due to the growing need for minimally invasive drug delivery systems and the concern of causing pain and anxiety in patients using a conventional hypodermic needle, localized, and generally pain-free delivery systems for therapeutics, such as resorbable microneedle (RMN) patches and hollow microneedle (HMN) arrays have been developed. Since the growth of the microelectronics industry in the 1990's and the success of microneedle fabrication and transdermal drug administration in 1998, the development of micromolding techniques for dissolving polymeric microneedle fabrication has enhanced the payload of delivery systems, prompting researchers to expand the repertoire of microneedle therapeutic uses.

Figure 4A:
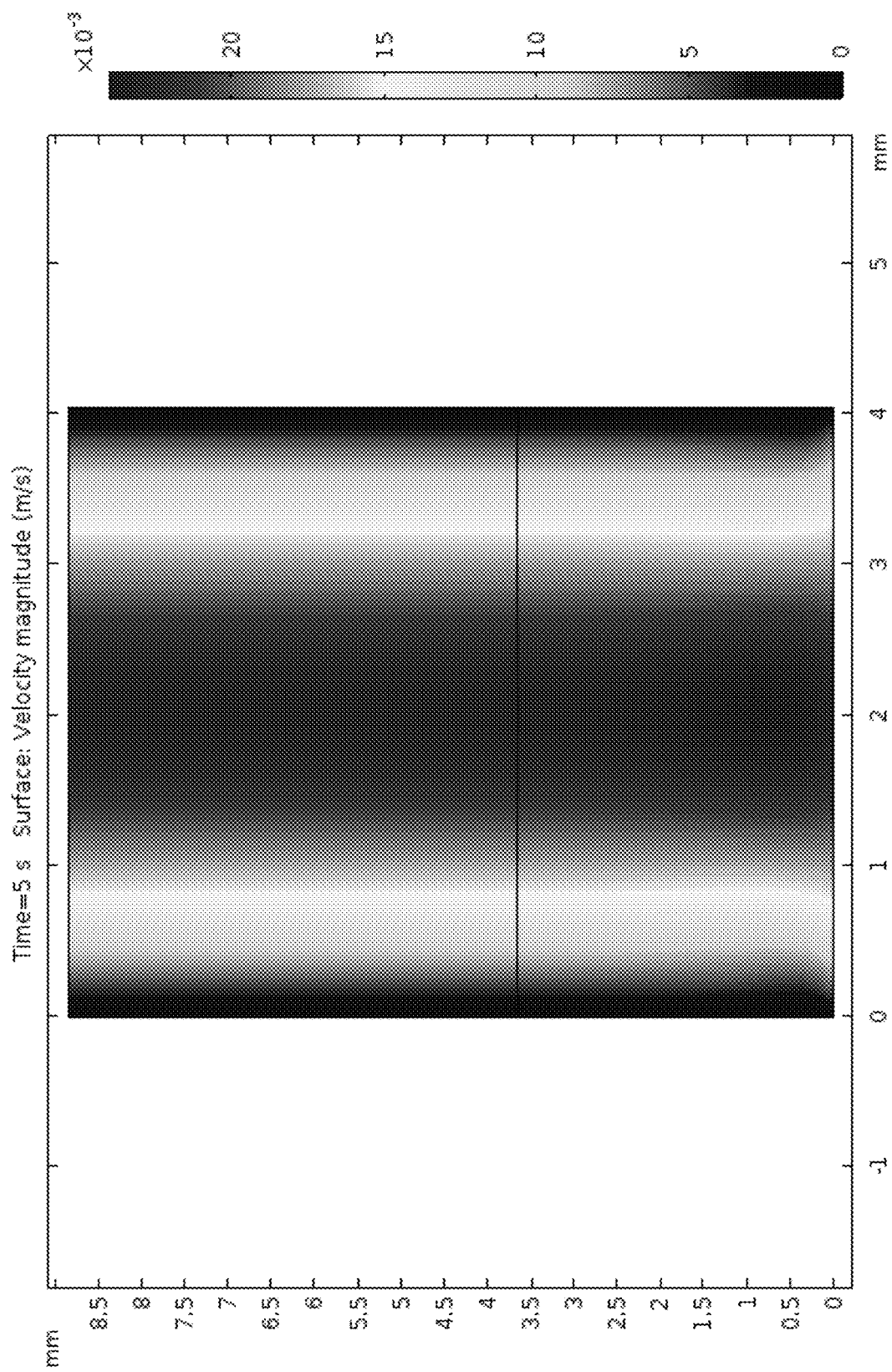
Figure 4B:
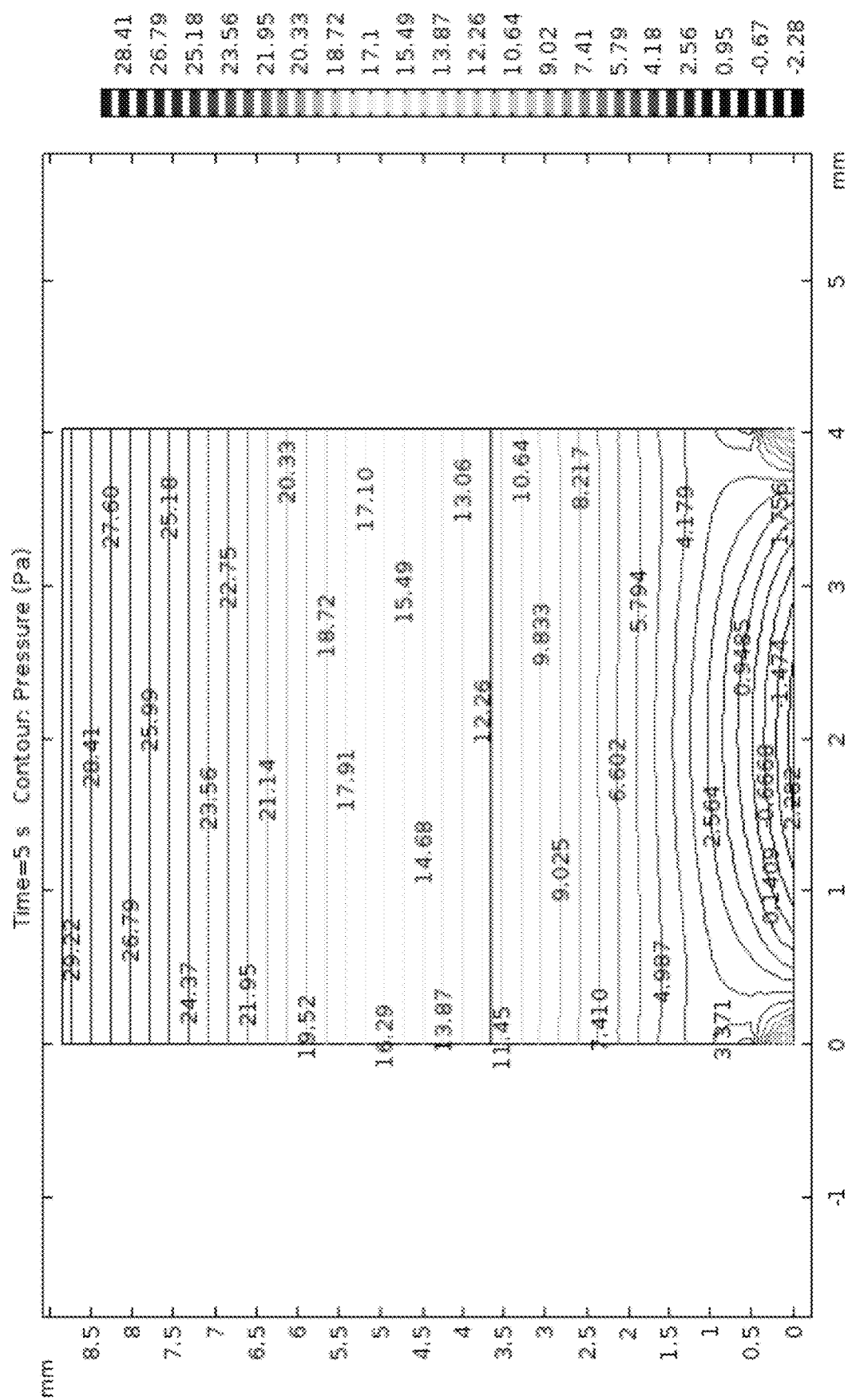
Figure 4C:
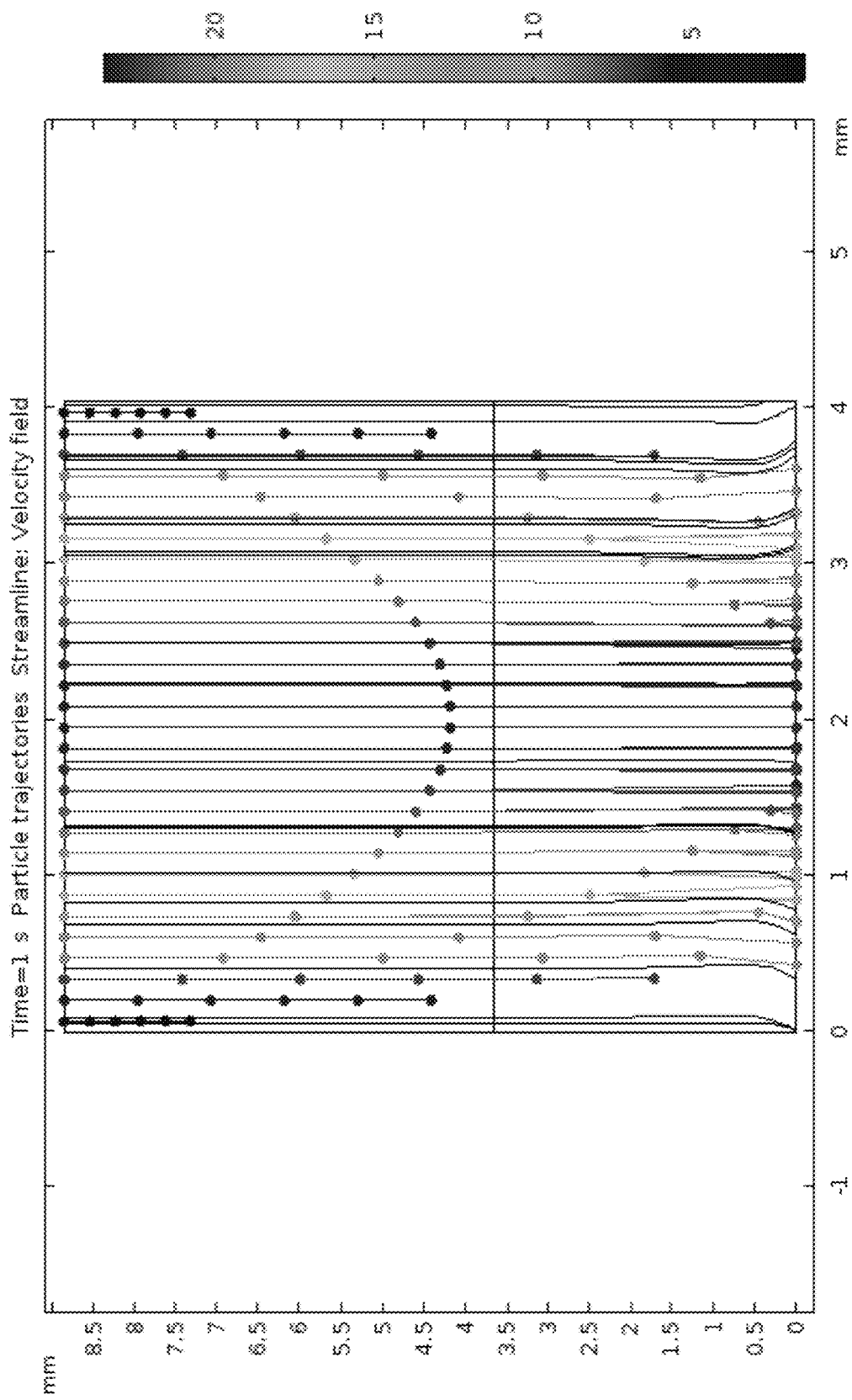
Figure 4D:
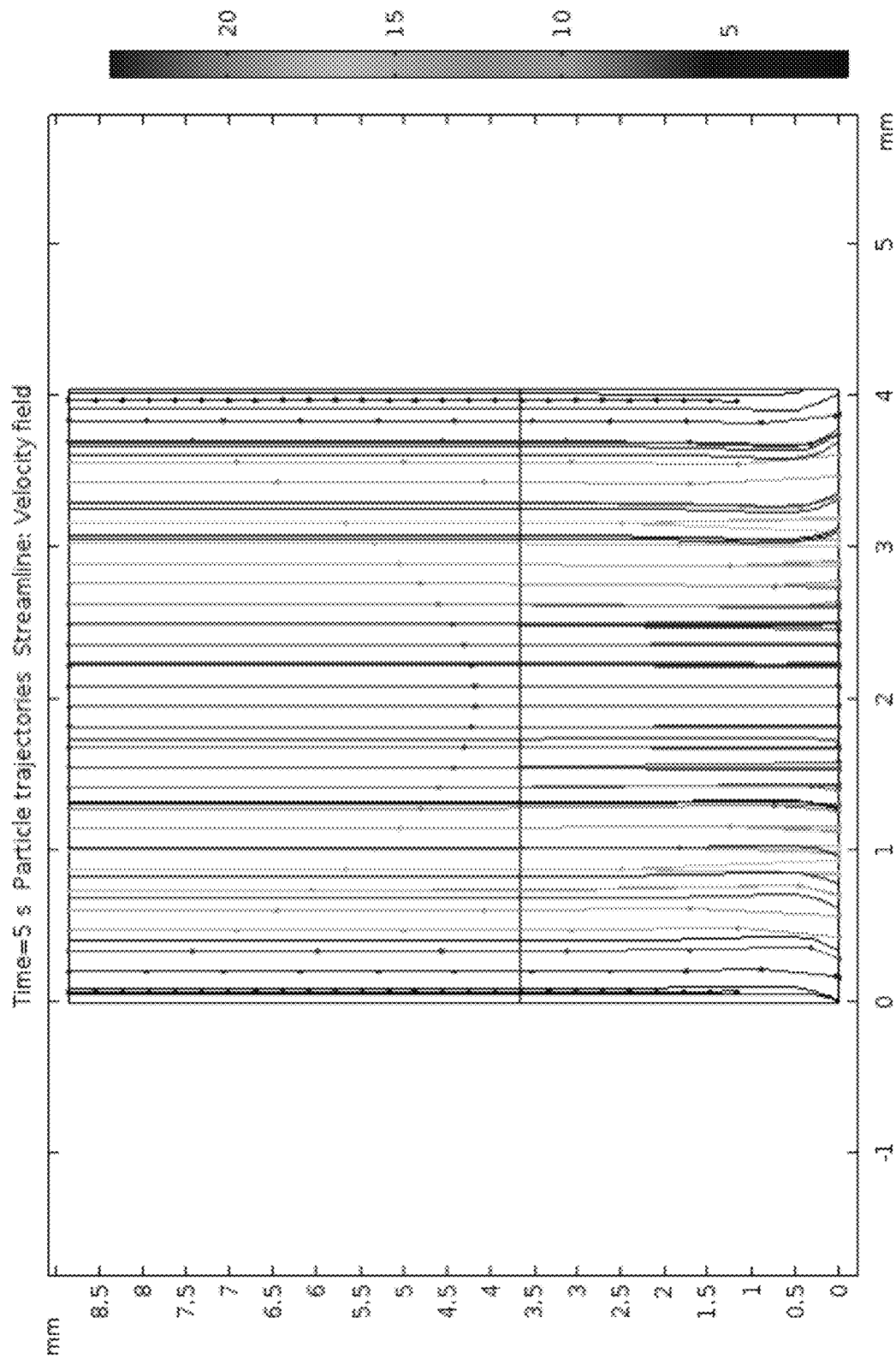

However, the current state of the art of using microneedles for drug delivery still has challenges. For example, one of the current challenges are micro and nanoscale-induced aggregation of microcapsule-based biocolloid suspensions. In vivo, the extent of aggregation of these biocolloids has been linked to an array of non-therapeutic scenarios namely, diffusive co-transport, partitioning-controlled micro gradients, chemotaxis and premature membrane biorerosion. During delivery, orifice blockage, capsule burst and premature cell release may result if the resilience of the particles is exceeded. The present invention addresses some of the problems by providing a new delivery mechanism using microneedles for drug delivery.

SUMMARY OF THE INVENTION

A 3D printed biocompatible drug delivery device is provided having a fluid delivery channel distinguishing three segments and a receiving chamber with an array of microneedles. The three segments of the delivery channel are stagnation zones before a drug is extruded and whereby an inverted funnel provides an increasing extrusion surface servicing the drug to the array of microneedles.

The first segment of the fluid delivery channel is a funnel with a diameter suitable to receive a syringe. The second segment of the fluid delivery channel is a cylinder connected to the smallest diameter of the funnel. The diameter of the cylinder matches the smallest diameter of the funnel. The third segment of the fluid delivery channel is an inverted funnel connected to the other side of the cylinder at the smallest diameter of the inverted funnel. The diameter of the smallest diameter of the inverted funnel matches the diameter of the cylinder. The inverted funnel diverges with an angle ranging from 10 to 45 degrees.

The receiving chamber has an array of microneedles located at its bottom. Each microneedle protrudes with an orifice (in one example a conical orifice) from the bottom surface of the receiving chamber. A section of the top surface of the receiving chamber fluidically connects to the bottom surface of the fluid delivery channel such that the array of microneedles matches up with the largest diameter of the inverted funnel to receive a drug delivered via the syringe and through the fluid delivery channel.

In one embodiment, the fluid delivery channel is centrally located in a cylindrical casing and the diameter of the cylindrical casing matches the diameter of the receiving chamber forming a nice package.

Embodiments of this invention have the following advantages:

- The embodiments provide a custom 3D printed HMN biodevice with a fluid delivery channel and an array of microneedles, which in one example have 13 conical frusta.
- The embodiments can be fabricated using the sustainable low-cost method of sterelolithography (SLA).
- By modifying the design of the flow-related components the challenge of colloidal stability associated with multi-phase formulations leading to nozzle blockage was circumvented.
- Qualitative screening cytotoxicity tests pre and post-extrusion through the drug delivery device using mammalian cells rule out cytotoxicity and outline equivalent viability to control treatments.
- The biocompatibility results suggest that the fluid delivery design, the photoresin selected as well as the fabrication and sterilization may be extended over a range of regenerative medicine and drug delivery applications.

BRIEF DESCRIPTION OF THE DRAWINGS

FIG. 1 shows according to an exemplary embodiment of the invention a process flow steps of device fabrication, cell encapsulation, and microcapsule extrusion.

FIGS. 2A-D shows according to an exemplary embodiment of the invention drawings of a 3D printed device with corresponding dimensioning. FIGS. 2A-B show the receiving chamber (bottom layer of the drug delivery device) with an array of 13 hollow microneedles with the array at the bottom surface of the receiving chamber. FIGS. 2C-D show the casing of the fluid delivery channel as well as the fluid delivery channel differentiating its three segments. Specifically, FIG. 2D is a side view of drug delivery device illustrating the fluid delivery channel centrally located in its casing with at the bottom the receiving chamber and its array of microneedles.

FIGS. 3A-D show according to an exemplary embodiment of the invention simulations of flow through the fluid delivery channel when an inverted funnel ((h5, d5, d7=3.67 mm) is incorporated in the design. The modeling of particle settling during reservoir filling at steady state with a laminar flow profile (FIG. 3A) and the corresponding pressure distribution contour plot (FIG. 3B). In parallel the unsteady state microcapsule release profile streamlines during continuous perfusion prior to extrusion are presented at times 1 s (FIG. 3C) and 5 s (FIG. 3D).

FIGS. 4A-D show according to an exemplary embodiment of the invention similarly as in FIGS. 3A-D, simulations of flow through the fluid delivery channel when a cylinder ((h5+h6), d6, d7=0) is incorporated in the design. The modeling of particle settling during reservoir filling at steady state with a laminar flow profile (FIG. 4A) and the corresponding pressure distribution contour plot (FIG. 4B).

In parallel the unsteady state microcapsule release profile streamlines during continuous perfusion prior to extrusion are presented at times 1 s (FIG. 4C) and 5 s (FIG. 4D).

DETAILED DESCRIPTION

In one embodiment, the design of the microneedle drug delivery device has two parts (FIGS. 2A-D): a fluid delivery channel stacked on top of a receiving chamber, respectively the top layer and bottom layer. The receiving chamber contains an array of microneedles. The fluid delivery channel differentiates three segments: a first funnel, a cylinder, a second funnel which is called the inverted funnel. In this first embodiment, each of the two parts can be printed using a 3D printer as two single parts which can then be glued together. In another embodiment, the microneedle device is a 3D printed device printed as a single device yet still distinguishing the receiving chamber with the array of microneedles and the fluid delivery channel.

Figure 1:
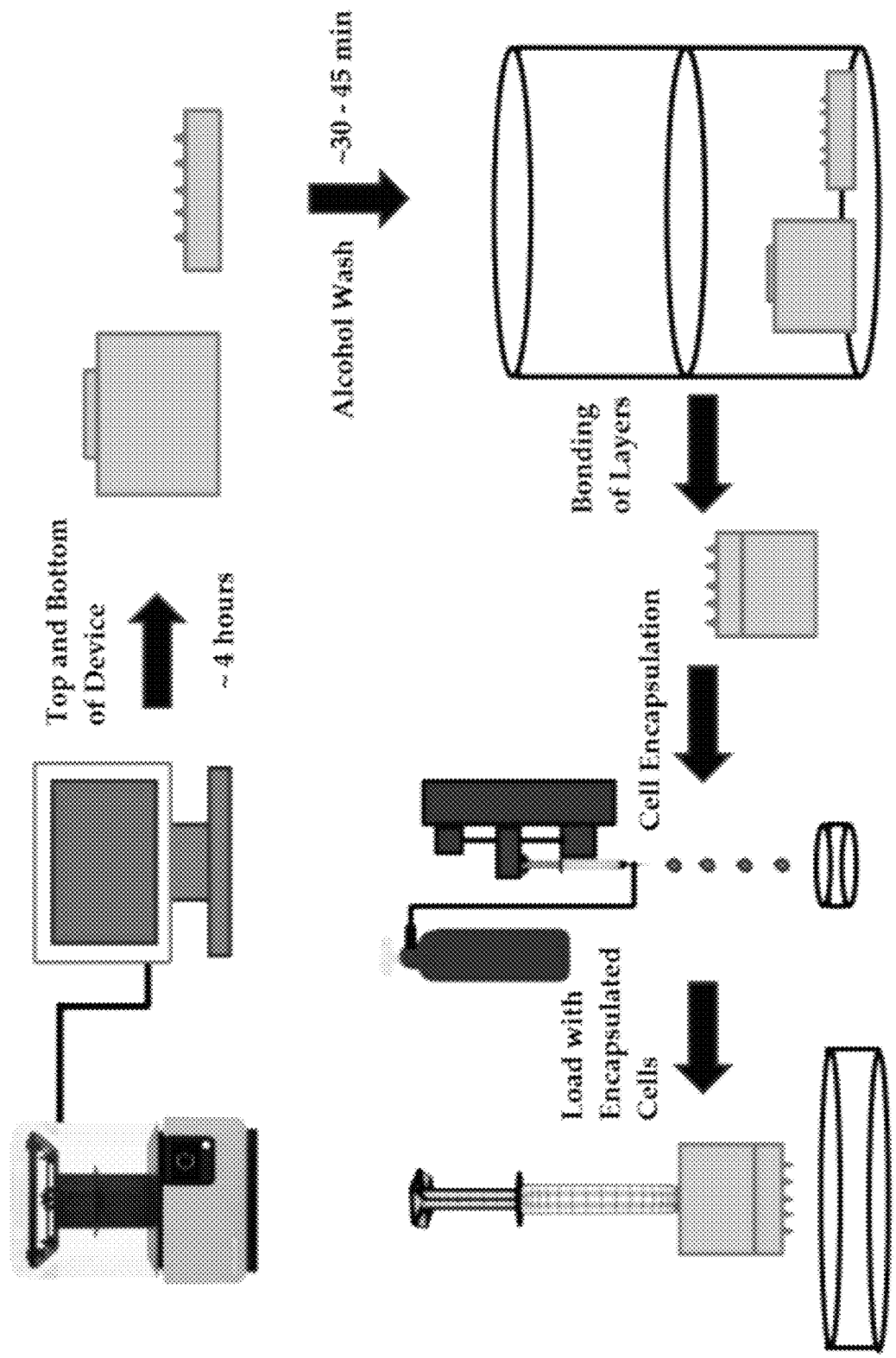
Figure 2A:
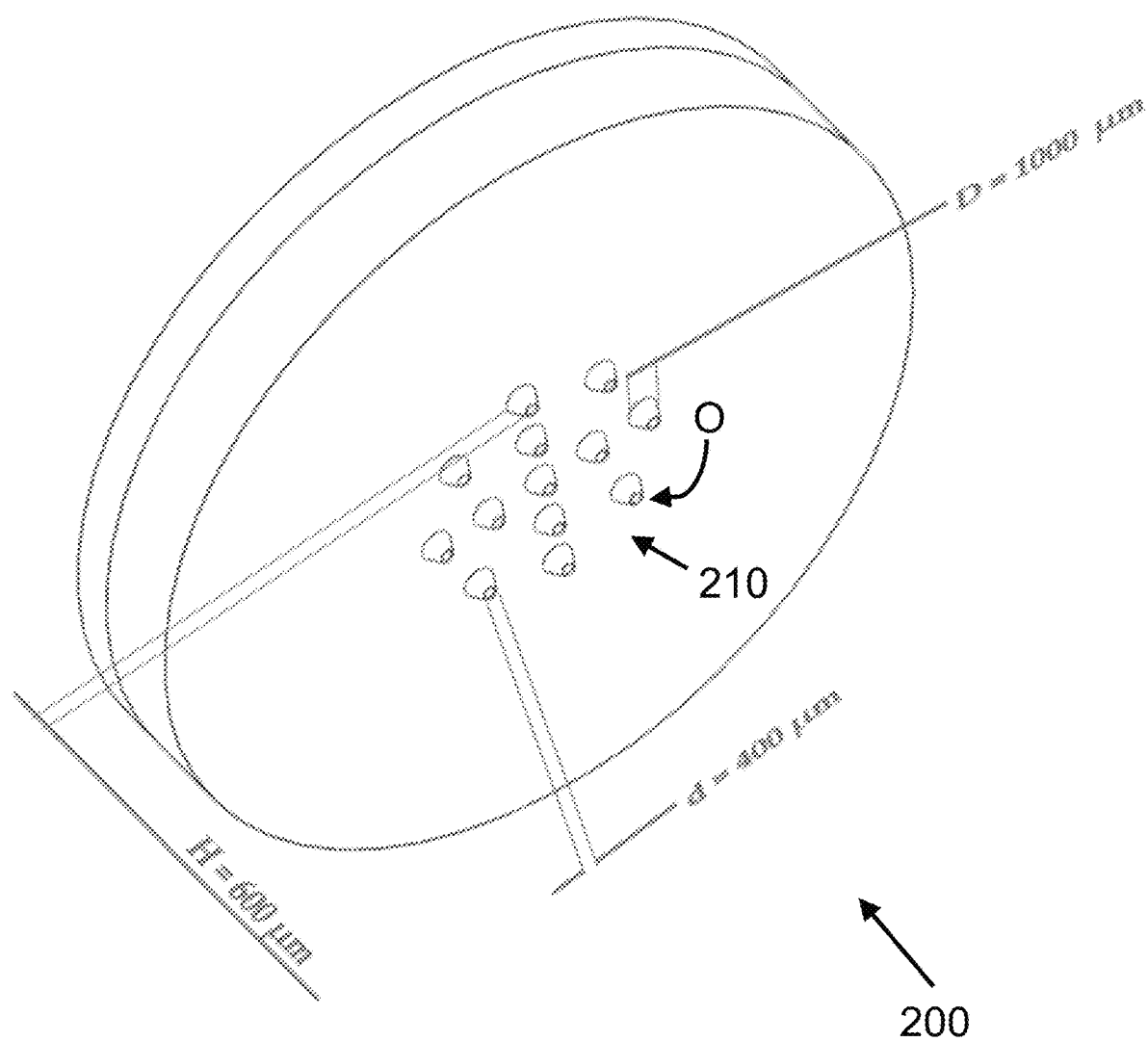
Figure 2B:
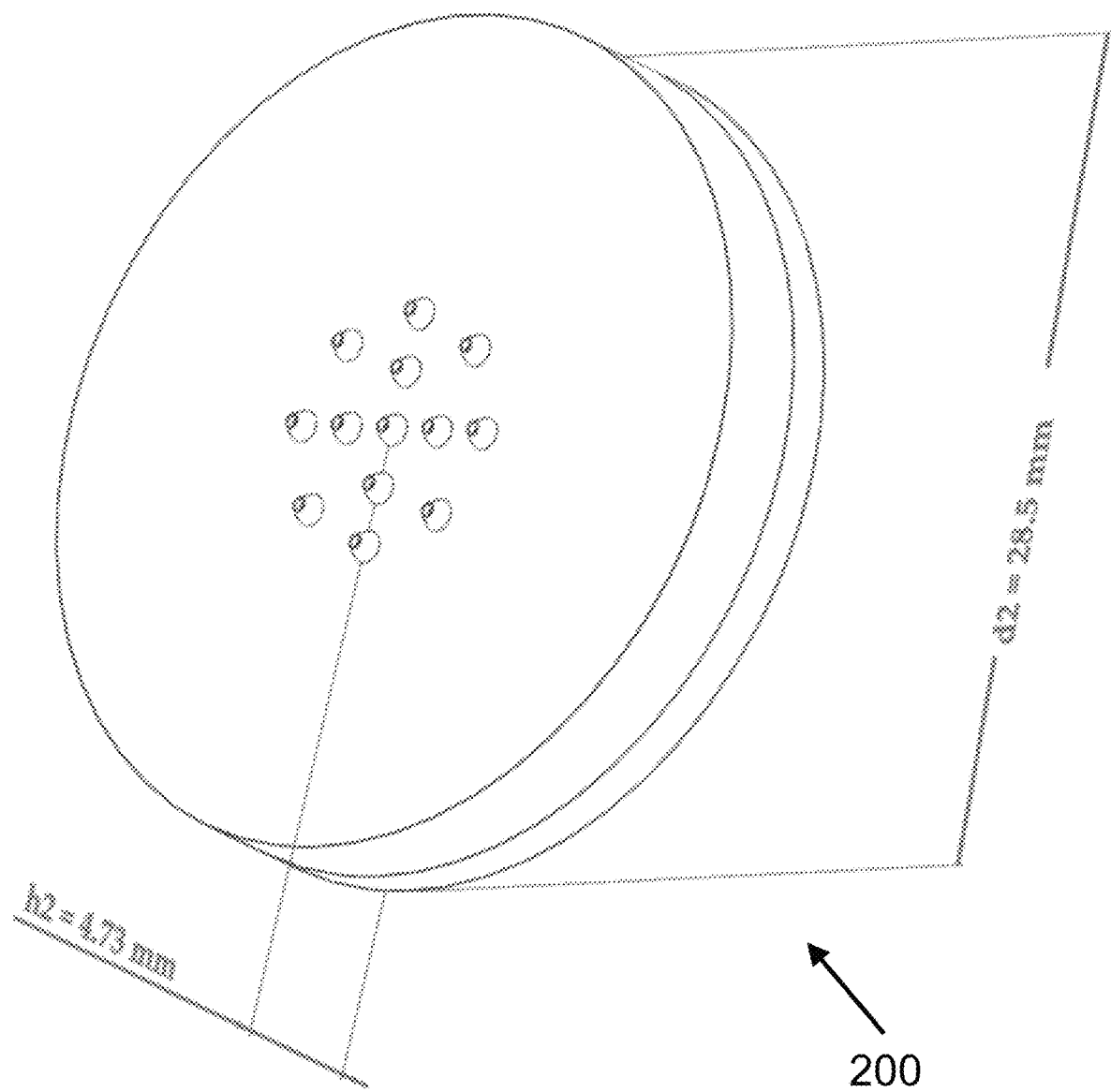
Figure 2C:
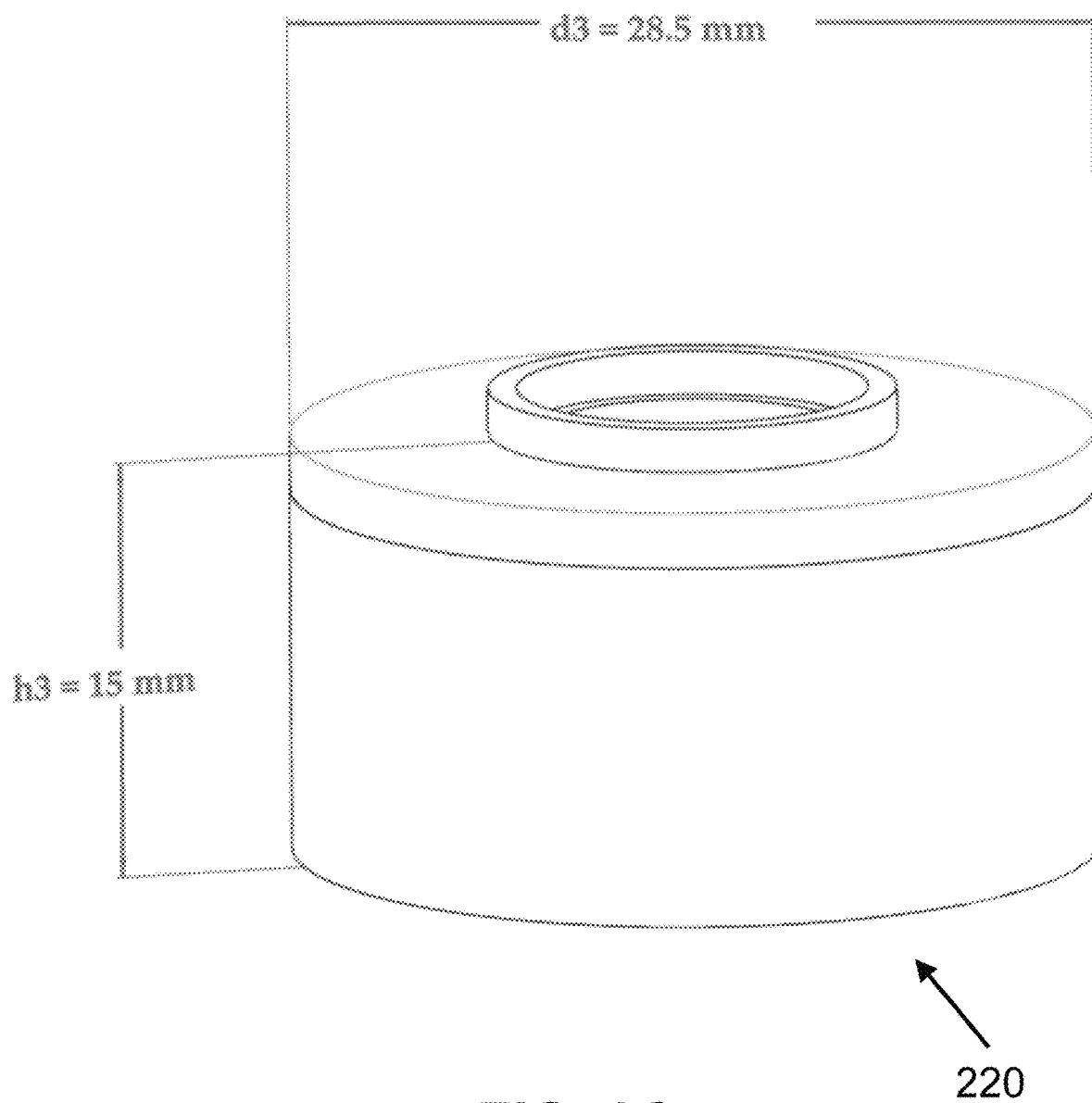
Figure 2D:
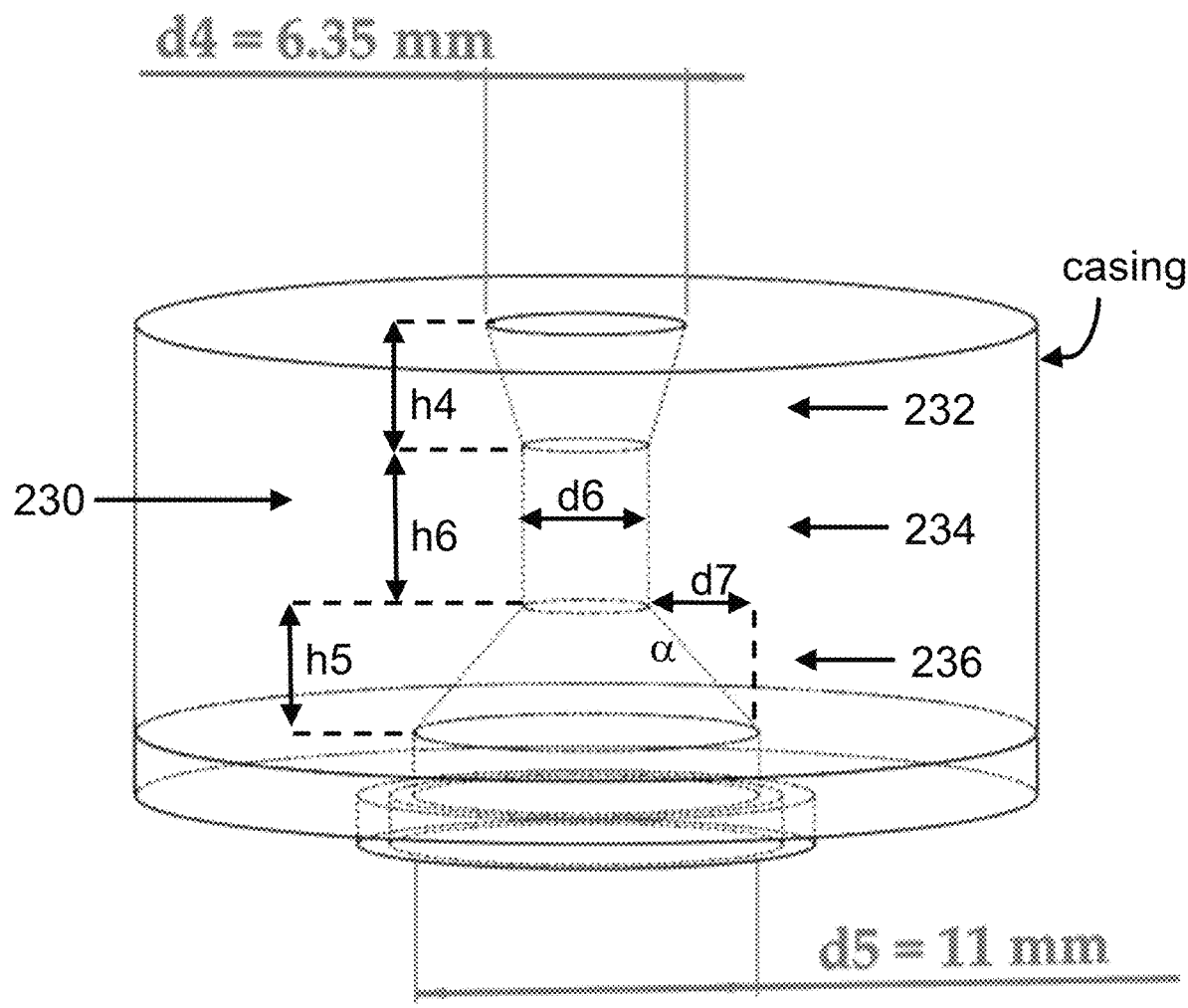
Figure 2D:
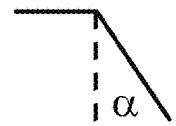

The fluid delivery channel can be centrally situated in a cylindrical casing (see FIG. 2D). Likewise, the receiving chamber could have a similar cylindrical casing. Any type of casing shape can be used as long as the delivery channel can be positioned in line with the array of microneedles (FIGS. 2A-D).

The type of material used for 3D printing should be a biocompatible material, such as, for example, but not limited to, a single photoresin formulation producing a resolution of 25 micrometers. The exact composition of the Clear FLGPCL02 methacrylate-based photoresin is proprietary. Distinguishable by clarity, the following is a non-exhaustive list of medical grade resins: dimethacrylate (DMA), polymethylmethacrylate (PMMA), and Methyl methacrylate/acrylonitrile/butadiene styrene (MABS). Methacrylate-based monomers used in bone cements dental fillings are considered to be biocompatible short term. The same conclusion has been drawn based on biocompatibility studies supporting this invention, where the viability of control treatment of cells was statistically equivalent to the ones exposed to the photoresin. Specifically, a 24 h cytotoxicity was conducted using adherent U87 mammalian cells in contact with a 3D printed slab and microencapsulated HepG2 (human hepatocellular carcinoma cells) were extruded through the microneedle assembly, both fabricated using stereolithography 3D printing of the Clear FLGPCL02 photoresin. The above biocompatibility results suggest that there is no undesired leaching of monomer material, mandatory regulatory criteria for the HMN device classified into the Class I external surface device by the FDA.

During the 3D printing process, UV light is directed through the window on the bottom side of the printer and selectively cured each cross-section. The microneedle device is orientated so that the microneedle orifices would be perpendicular to the support system. This orientation is possible due to their small dimensions, had the orifices of the microneedles been larger and more susceptible to collapse, they would have to be oriented at an angle to reduce the surface area of each cross-section. Once the parts are successfully printed, the parts are placed in an alcohol bath to ensure quality resolution. Specifically, in one example, the parts are placed in isopropyl alcohol (IPA, 70% v/v)), bathed for 20-30 min (10-15 min in tank 1, 10-15 min in tank 2), and then placed in a UV unit for 15 min for post-curing and removal of the uncured resin by leaching.

Prior to the assembly of the top and bottom parts of the device, the parts are soaked in ethanol (70% v/v) followed by three rinses in sterile DI water. The top and bottom part of the device are mounted in a sterile environment using a silicone-based sealant GE Silicone II* Caulk, (General electrics, Boston, Mass., USA). The parts to be sealed are maintained at 50 psi for 30 min.

FIG. 2A shows an example of a 3D printed circular receiving chamber/casing 200 with an array of 13 hollow microneedles 210. The number is microneedles in the array is optional and drug delivery application specific. Each microneedle protrudes from the bottom surface with a height of H. In this specific example H is 600 micrometers. The microneedle is tapered with a diameter D of 1000 micrometers at the bottom of the microneedle array part, and a diameter d of 400 micrometers at the tip. The orifice O (inner diameter) of each microneedle is set at 50 microns less the d, by maintaining the wall thickness of the frustrum constant at 25 μm.

FIG. 2B shows the height h2 of the receiving chamber 200 of 4.73 mm and a diameter d2 of 28.5 mm.

FIG. 2C shows an example of a 3D printer the top layer 220 (casing with centrally located the fluid delivery channel) with a height h3 of 15 mm and a diameter d3 of 28.5 mm. Preferably d2 and d3 would have similar dimensions. Top layer 220 contains, more or less centrally oriented, the fluid delivery channel 230. The fluid delivery channel has an inner fluid reservoir that, in this example is characterized by a volume of 0.5 mL. As shown in FIG. 2D, the fluid reservoir 230 has a first funnel 232 which is sized to receive a syringe (not shown). First funnel 232 has a height h4 of 98 mm. The diameter d4 of the opening of first funnel 232 is, in this example, 6.35 mm converging to a cylinder 234 with a diameter d6 of 4.04 mm and a height h6 of 5.19 mm. Cylinder 234 is then connected to the second funnel, which is the inverted funnel 236. Inverted funnel 236 diverges from the diameter d6 of cylinder 234 to an opening diameter d5 of 11 mm in this particular example. The height h5 of the inverted funnel 236 is 3.67 mm. It is noted that the dimensions of the microneedle array 210 fits within the opening diameter d5 of inverted funnel 236 so that the fluid/drug that is ejected from the syringe flows through the fluid delivery channel and reaches all the microneedles. Specifically, it is noted that the design of the fluid delivery channel, especially the inverted funnel, is intentional to control the flow rate of the fluid/drug from the syringe towards the microneedles and then into the skin of a person. Higher administration flow rates are associated with patient discomfort while lower flowrates may be conducive to nozzle blockage depending on the formulation.

In general, a range for following ranges or nominal dimensions could be used subject to printing and post-printing shrinkage resolution:

H 600-750 micrometers
D 900-1250 micrometers
d 200-500 micrometers
50 micrometers (diameter)
h2 4.73 mm
d2 28.5 mm
d3 28.5 mm
h3 15 mm
d4 6.35 mm
h4 2.98 mm
d5 11 mm
h5 3.67 mm
d6 4.04 mm
h6 5.19 mm
d7 equals [(d5 minus d6)/2] where d7 ranges from 3.67 mm for an angle of 45 degrees to zero for an angle of zero. However, at zero d7 would conform to a cylinder extending cylinder 234 which defeats the purpose of the objectives of this invention. With that the angular range (α see FIG. 2D) of the inverted funnel 236 would range from 10 to 45 degrees, with d7 ranging from 0.642-3.67 mm, respectively.

To test the microneedle drug delivery device and its applicability to cell-hydrogel based therapies for wound healing a study was conducted to assess the viability of human hepatocellular carcinoma (HepG2) cells immobilized in atomized alginate capsules (3.5% (w/v) alginate, d=225 micrometers±24.5 micrometers) post-extrusion through a 3D printed methacrylate-based hollow microneedle assembly (circular array of 13 conical frusta) fabricated using stereolithography and according to the specifications described herein. With a jetting reliability of 80%, the solvent-sterilized device with a root mean square roughness of 158 nm at the extrusion nozzle tip (d=325 micrometers) was operated at a flowrate of 12 mL/min. There was no significant difference between the viability of the sheared and control samples for extrusion times of 2 h (p=0.14, α=0.05) and 24 h (p=0.5, α=0.05) post-atomization. Factoring the increase in extrusion yield from 21.2% to 56.4% attributed to hydrogel bioerosion quantifiable by a loss in resilience from 5470 (J/m$^3$) to 3250 (J/m$^3$), there was no significant difference in percentage relative payload (p=0.2628, α=0.05) when extrusion occurred 24 h (12.2±4.9%) when compared to 2 h (9.9±2.8%) post-atomization. Results, which are shown in detail in Appendix A of the US provisional application to which this application claims priority, highlight the feasibility of encapsulated cell extrusion, specifically protection from shear, through a hollow microneedle assembly.

To enable flowrate for therapeutic administration, the dimensions of the 3D printed were varied to generate a range of aspect ratios. The following are successful 3-D printed designs labeled according to the following convention [D,d, H] where the dimensions are in μm pre-shrinkage (referring to FIG. 2A: [900,300,600], [1000,400,600], [1100,500,600], and, [1250,400,750].

The minimum injection volume for the microneedle device is 0.5 ml of microcapsules for a 45 degree inverted funnel design (a). Depending on particle count, the cross-linked hydrogel-based microcapsules suspension ranging from 50 micrometers to 350 micrometers in size which are characterized by a dynamic viscosity and density ranges 1 cP-30 cP and 1 g/cm$^3$-1.7 g/cm$^3$, respectively. The administration ranged from 0.3-12 mL/min, where the lower flowrates coincided with nozzle blockage, while the higher flowrates yielded an extrusion yield of between 21.2% and 51.6% corresponding to hydrogel bioerosion quantifiable by a loss in resilience from 5470 (J/m$^3$) to 3250 (J/m$^3$).

Figure 3A:
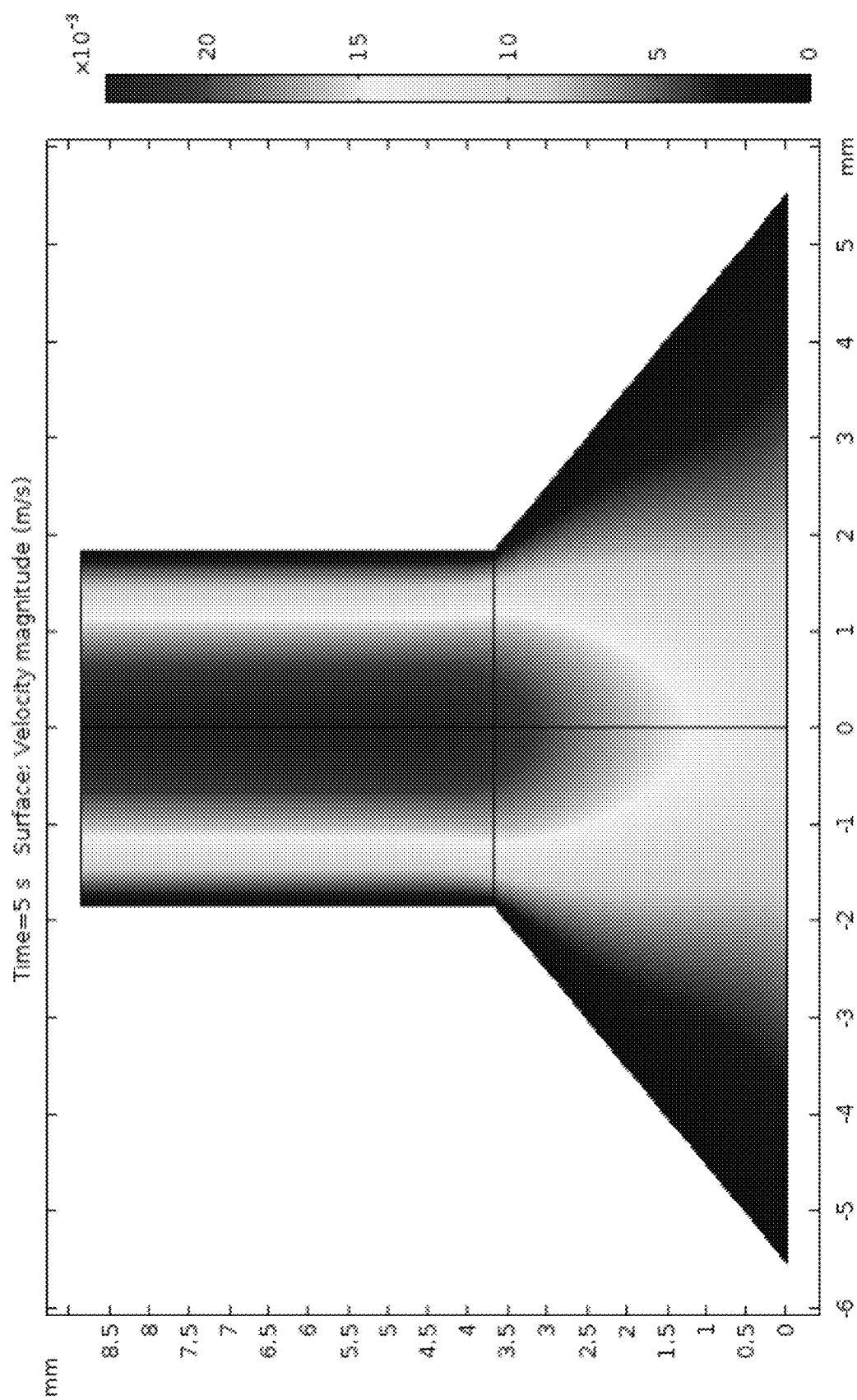
Figure 3B:
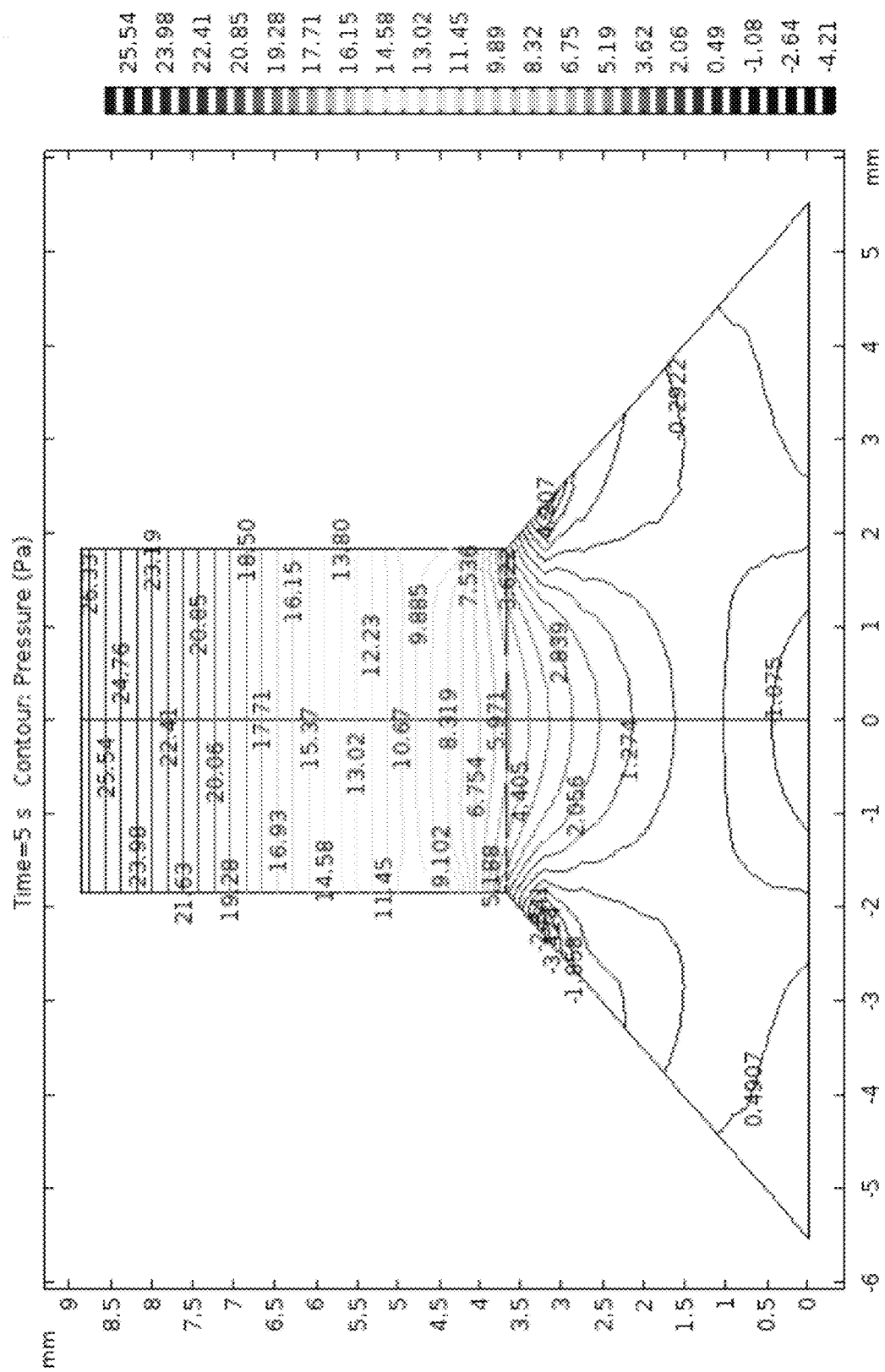
Figure 3C:
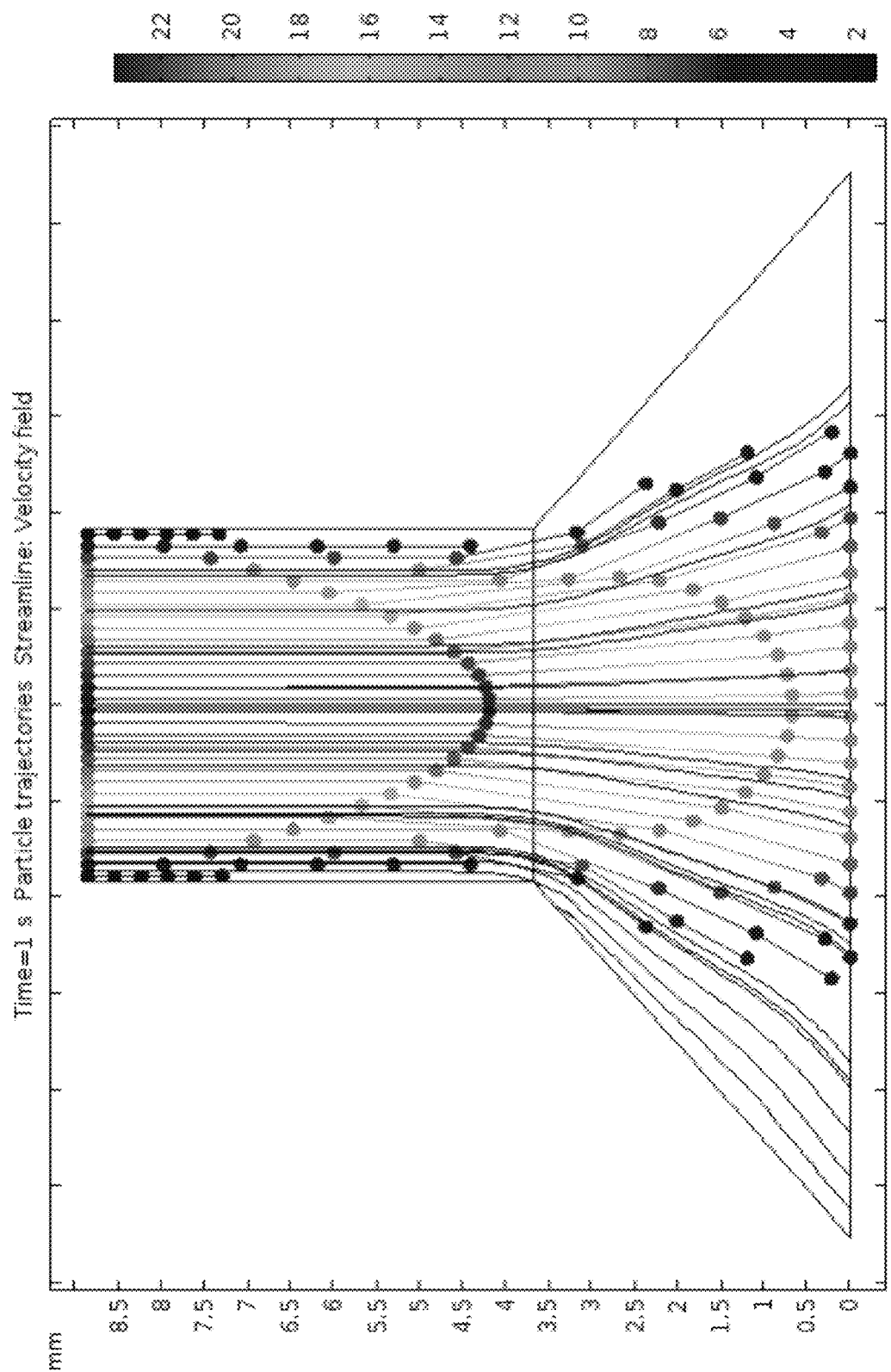
Figure 3D:
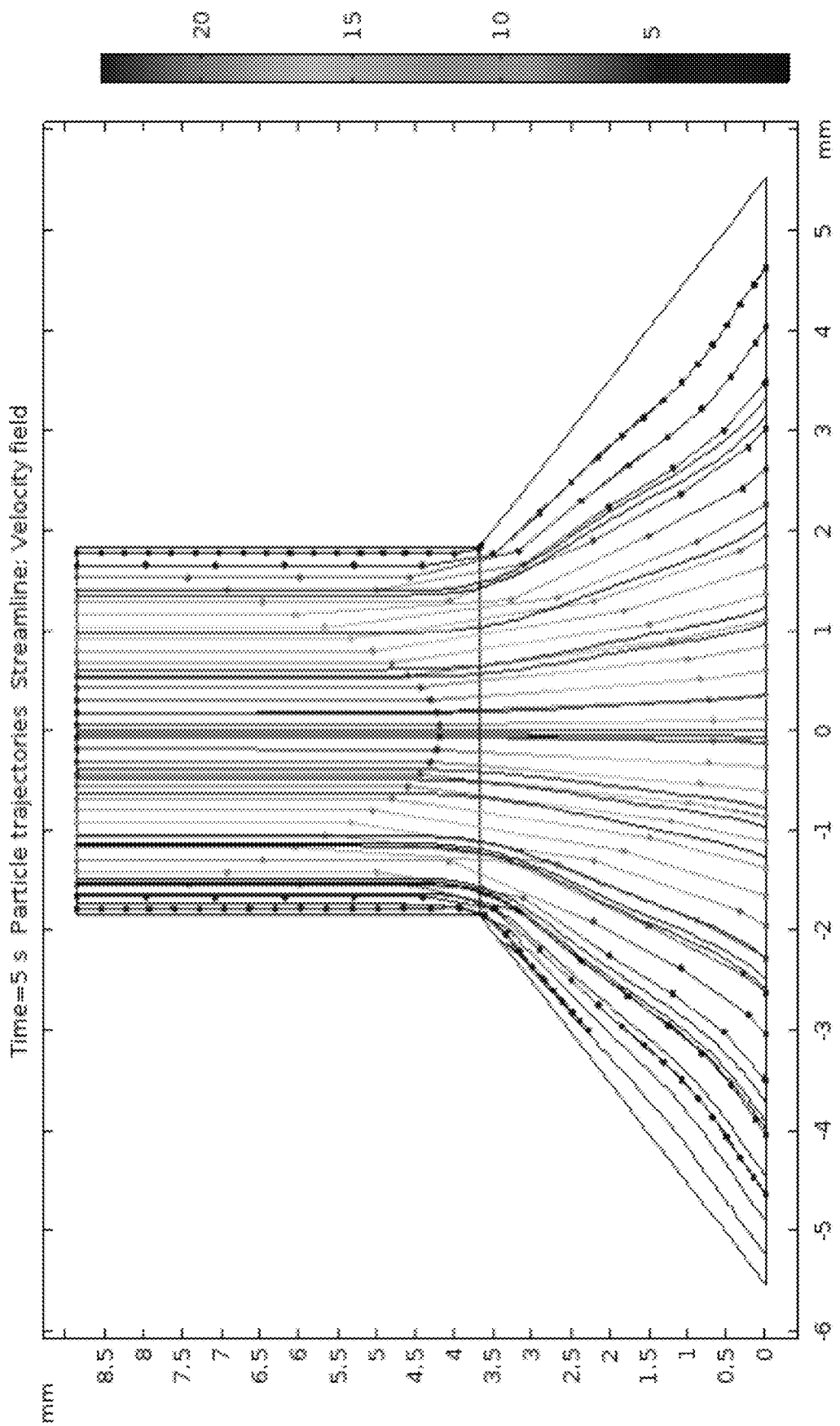

Colloidal stability may be inferred by surface coating of microcapsules with a polyelectrolyte, changing the ionic strength of the suspension media and varying the size of the capsules. Changing any or all of these factors may constrain the therapeutic range. Flexible design of the delivery channel dictated by geometry may circumvent the above-stated formulation challenges. By changing the design of the fluid delivery channel from a simple cylindrical structure to the fluid delivery channel with an inverted funnel serving the array of microneedles as shown in FIG. 2D, an optimal compromise between the particle settling time and effective administration rates is reached. Specifically, by creating stagnation zones of the fluid delivery channel as shown in FIGS. 4C-D before extrusion through the orifices of the microneedles, the settling particle density due to laminar flow is distributed on a larger surface area as compared to a pure cylindrical structure where the entire particle mass to be extruded settles on the extrusion surface blocking the pores (FIGS. 3C-D).

By changing the design of the fluid delivery channel from a simple cylindrical structure (FIGS. 4A-D) to an inverted funnel (FIGS. 3A-D), an optimal compromise between the particle settling time and effective administration rates may be reached. Specifically, by creating stagnation zones shown in the contour plot (FIG. 3B), the settling particle density due to laminar flow is distributed on a larger surface area (invention) as compared to the pure cylindrical structure where the entire particle mass to be extruded settles on the extrusion surface (FIG. 4B) blocking the pores. This difference is also reflected in the trajectory streamlines where the majority of the microcapsules that have reached the bottom of the channel (h5=0 mm) have velocity of approximately 14 mm/s (FIGS. 3C-D) as compared to 20 mm/s (FIGS. 4C-D) for the inverted funnel and cylindrical designs, respectively.

What is claimed is:

1. A biocompatible drug delivery device, comprising:
    (a) a fluid delivery channel distinguishing three segments, a first segment, a second segment and a third segment, wherein the fluid delivery channel is fitted within a fluid delivery casing,
        wherein the first segment is a funnel with a diameter suitable to receive a syringe,
        wherein the second segment is a cylinder connected to a smallest diameter of the funnel, and wherein a diameter of the cylinder is equal to the smallest diameter of the funnel,
        wherein the third segment is an inverted funnel connected to an opposite side of the cylinder at a smallest diameter of the inverted funnel,
        wherein the diameter of the smallest diameter of the inverted funnel is equal to the diameter of the cylinder, and
        wherein the inverted funnel diverges with an angle ranging from 10 to 45 degrees; and
    (b) a receiving chamber comprising at a bottom of the receiving chamber an array of microneedles,
        wherein each microneedle protrudes with an orifice from a bottom surface of the receiving chamber,
        wherein a section of a top surface of the receiving chamber fluidically connects to a bottom surface of the fluid delivery channel such that the array of microneedles is in fluid communication with a largest diameter of the inverted funnel to receive a drug delivered via the syringe and through the fluid delivery channel,
    wherein the biocompatible drug delivery device is a 3D printed and biocompatible device, and
    wherein the three segments of the fluid delivery channel are stagnation zones before a drug is extruded and whereby the inverted funnel provides an increasing extrusion surface servicing the drug to the array of microneedles.

2. The biocompatible drug delivery device as set forth in claim 1, wherein a diameter of the fluid delivery casing is greater than or equal to a diameter of the receiving chamber.

3. The biocompatible drug delivery device as set forth in claim 1, wherein the fluid delivery casing is a cylindrical fluid delivery casing.

4. The biocompatible drug delivery device as set forth in claim 1, wherein the fluid delivery channel is centrally fitted within the fluid delivery casing.

5. The biocompatible drug delivery device as set forth in claim 1, further comprising a receiving chamber casing, wherein the receiving chamber is fitted within the receiving chamber casing.

6. The biocompatible drug delivery device as set forth in claim 5, wherein the receiving chamber casing is a cylindrical receiving chamber casing.

7. The biocompatible drug delivery device as set forth in claim 5, wherein the receiving chamber is centrally fitted within the receiving chamber casing.

8. The biocompatible drug delivery device as set forth in claim 1, further comprising a receiving chamber casing, wherein the receiving chamber is fitted within the receiving chamber casing, wherein the fluid delivery casing has a diameter that is equal to a diameter of the receiving chamber casing.

9. A biocompatible drug delivery device, comprising:
(a) a fluid delivery channel distinguishing three segments, a first segment with a first longitudinal axis, a second segment with a second longitudinal axis and a third segment with a third longitudinal axis, wherein the first longitudinal axis, the second longitudinal axis, and the third longitudinal axis are aligned with each other forming one common longitudinal axis,
wherein the first segment is a funnel with a diameter suitable to receive a syringe,
wherein the second segment is a cylinder connected to a smallest diameter of the funnel, and wherein a diameter of the cylinder is equal to the smallest diameter of the funnel,
wherein the third segment is an inverted funnel connected to an opposite side of the cylinder at a smallest diameter of the inverted funnel,
wherein the diameter of the smallest diameter of the inverted funnel is equal to the diameter of the cylinder, and
wherein the inverted funnel diverges with an angle ranging from 10 to 45 degrees; and
(b) a receiving chamber comprising at a bottom of the receiving chamber an array of microneedles,
wherein each microneedle protrudes with an orifice from a bottom surface of the receiving chamber,
wherein a section of a top surface of the receiving chamber fluidically connects to a bottom surface of the fluid delivery channel such that the array of microneedles is in fluid communication with a largest diameter of the inverted funnel to receive a drug delivered via the syringe and through the fluid delivery channel,
wherein the biocompatible drug delivery device is a 3D printed and biocompatible device, and
wherein the three segments of the fluid delivery channel are stagnation zones before a drug is extruded and whereby the inverted funnel provides an increasing extrusion surface servicing the drug to the array of microneedles.

10. The biocompatible drug delivery device as set forth in claim 9, further comprising a fluid delivery casing, wherein the fluid delivery channel is fitted within the fluid delivery casing.

11. The biocompatible drug delivery device as set forth in claim 10, wherein a diameter of the fluid delivery casing is greater than or equal to a diameter of the receiving chamber.

12. The biocompatible drug delivery device as set forth in claim 10, wherein the fluid delivery casing is a cylindrical fluid delivery casing.

13. The biocompatible drug delivery device as set forth in claim 10, wherein the fluid delivery channel is centrally fitted within the fluid delivery casing.

14. The biocompatible drug delivery device as set forth in claim 9, further comprising a receiving chamber casing, wherein the receiving chamber is fitted within the receiving chamber casing.

15. The biocompatible drug delivery device as set forth in claim 14, wherein the receiving chamber casing is a cylindrical receiving chamber casing.

16. The biocompatible drug delivery device as set forth in claim 14, wherein the receiving chamber is centrally fitted within the receiving chamber casing.

17. The biocompatible drug delivery device as set forth in claim 9, further comprising a receiving chamber casing, wherein the receiving chamber is fitted within the receiving chamber casing, further comprising a fluid delivery casing, wherein the fluid delivery channel is fitted within the fluid delivery casing, wherein the fluid delivery casing has a diameter that is equal to a diameter of the receiving chamber casing.

* * * * *